United States Patent [19]

Bogdanoff

[11] Patent Number: 4,568,282
[45] Date of Patent: Feb. 4, 1986

[54] DENTAL PATH OF INSERTION GUIDE

[76] Inventor: Steven P. Bogdanoff, 1125 S. University Dr., Plantation, Fla. 33324

[21] Appl. No.: 706,943
[22] Filed: Mar. 1, 1985
[51] Int. Cl.⁴ .............................................. A61C 19/04
[52] U.S. Cl. ....................................................... 433/72
[58] Field of Search ............... 433/74, 73, 75; 33/150, 33/147, 143 C, 192, 513, 514

[56] References Cited

U.S. PATENT DOCUMENTS

| | | | |
|---|---|---|---|
| 1,246,408 | 11/1917 | Fish | 33/192 |
| 1,726,193 | 8/1929 | Ross | 433/74 |
| 2,540,555 | 2/1951 | Slaughter, Jr. | 33/174 |
| 2,618,068 | 11/1952 | Apple | 33/21 |
| 2,665,488 | 1/1954 | Tobey | 33/148 |
| 2,851,728 | 4/1958 | Spalten et al. | 433/74 |
| 2,910,773 | 11/1959 | Walton | 32/67 |
| 3,417,471 | 12/1968 | Mitchell | 32/67 |
| 4,229,166 | 10/1980 | Cusato et al. | 433/72 |

Primary Examiner—Robert Peshock
Attorney, Agent, or Firm—Roylance, Abrams, Berdo & Goodman

[57] ABSTRACT

A dental path of insertion guide which provides visual comparison of tooth surfaces that have been prepared for bridgework. The guide can be straight, U-shaped, or arcuate, and has at least four pins supported for slidable movement thereon, which pins extend vertically upwardly or downwardly and are parallel. A removable cap is provided to facilitate addition or removal of pins from the guide.

14 Claims, 13 Drawing Figures

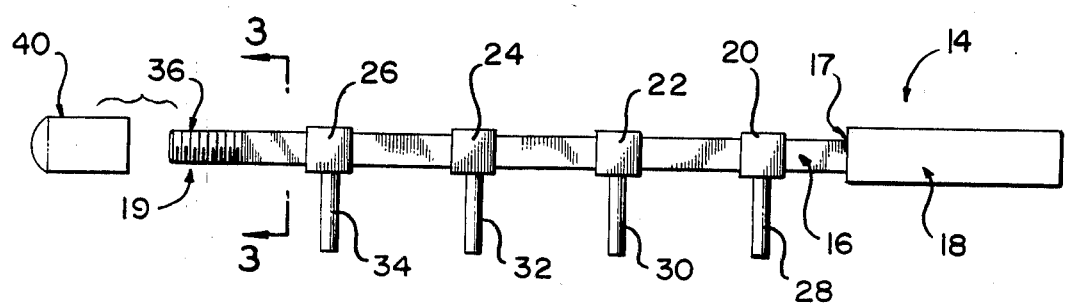
FIG. 1
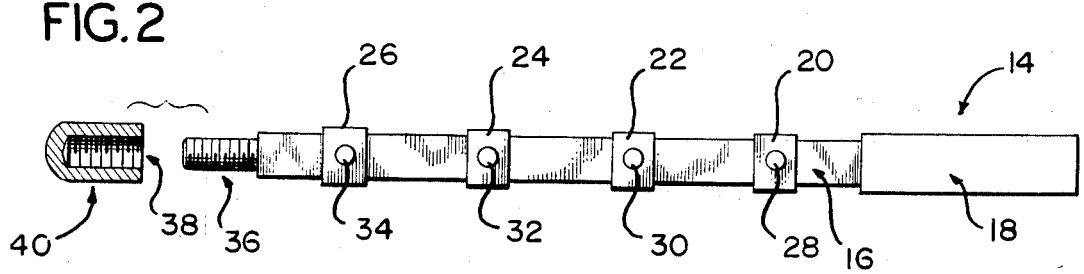
FIG. 2
FIG. 3 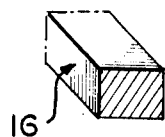 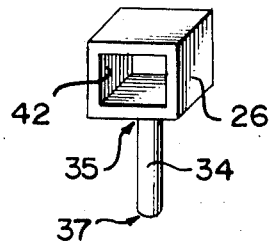 FIG. 4
FIG. 5
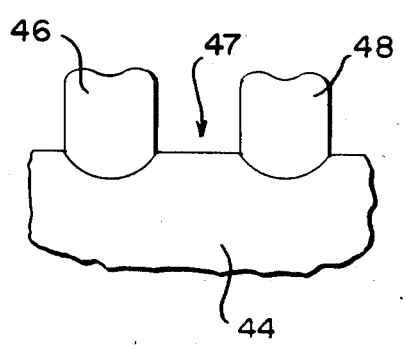
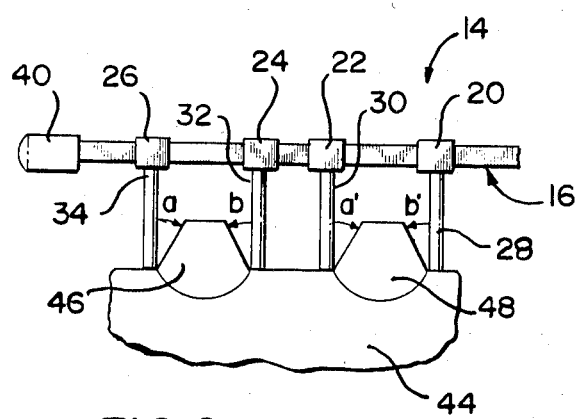
FIG. 6

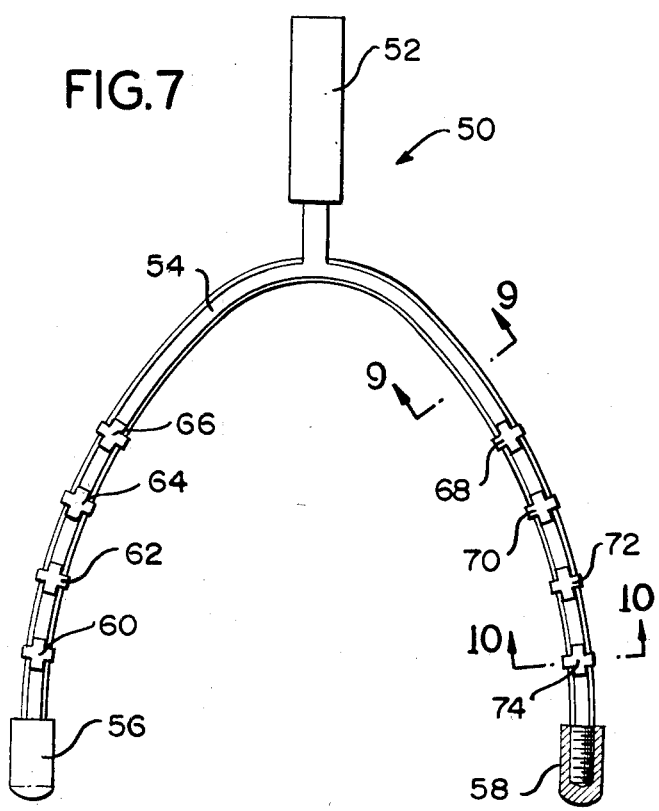
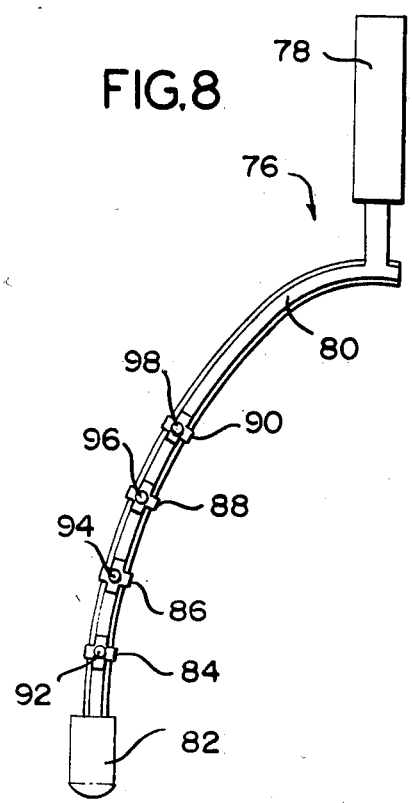
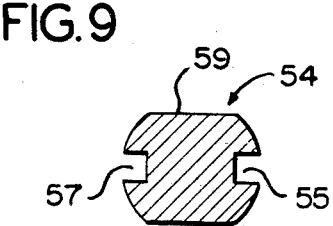
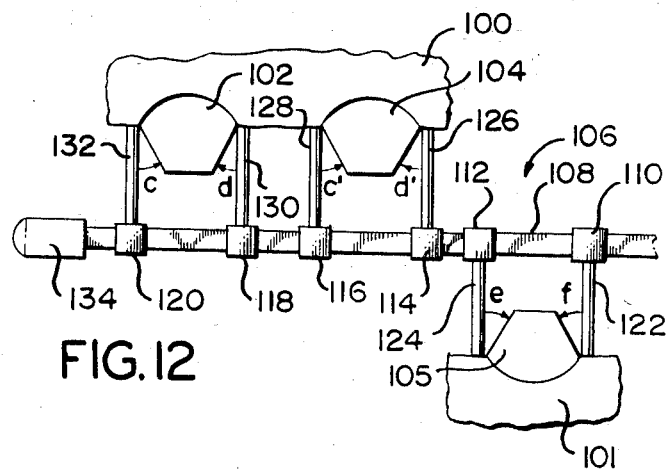
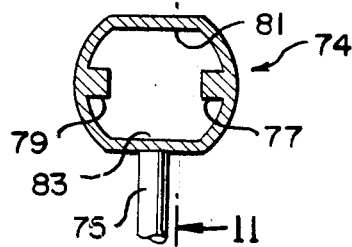
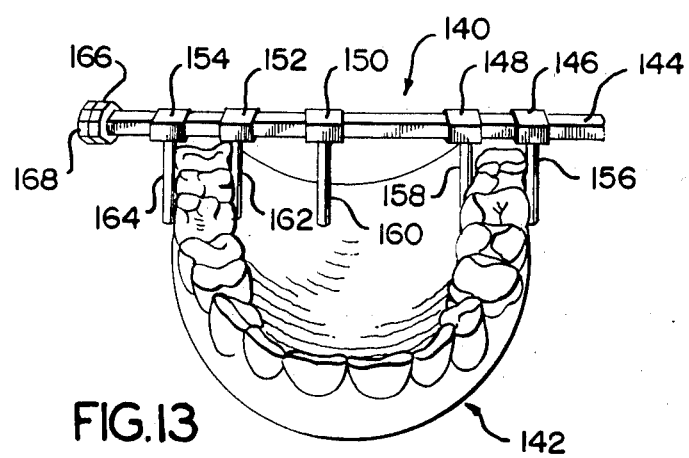
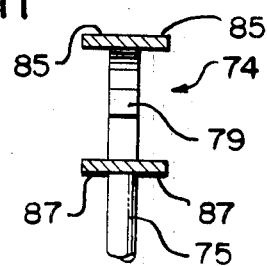

DENTAL PATH OF INSERTION GUIDE

FIELD OF THE INVENTION

This invention relates to devices for aiding dental practitioners in prosthetic work involving two or more teeth. More particularly, the invention relates to a path of insertion guide which can be used in the mouth before, during and after preparation of the teeth for restoration with splinted teeth, or multiple unit bridgework.

BACKGROUND OF THE INVENTION

Numerous attempts have been made to devise dental aides for prosthetic work. Among these are the following U.S. Pat. No.: 1,246,408 to Fish; U.S. Pat. No. 1,726,193 to Ross; U.S. Pat. No. 2,540,555 to Slaughter, Jr.; U.S. Pat. No. 2,618,068 to Apple; U.S. Pat. No. 2,665,488 to Tobey; U.S. Pat. No. 2,910,773 to Walton; U.S. Pat. No. 3,417,471 to Mitchell; and U.S. Pat. No. 4,229,166 to Cusato et al.

Many of these devices are "paralleling instruments", which contain pins that are rigidly affixed at a 90° angle to an elongated support. These devices are primarily used for placing precision attachments in laboratory models, or for making careful measurements for crown and bridgework.

These prior art devices, however, have numerous shortcomings which render them impractical in many situations encountered by dental practitioners.

For example, some of these devices can only be used for one or two teeth at a time. Others are restricted to use outside the mouth such as, for example, on plastered molds or laboratory models. Others are two bulky to be used in the posterior portions of the mouth. Another drawback is the inability to relate multiple surfaces of teeth to multiple surfaces of other teeth, such as top teeth to bottom teeth, front teeth to back teeth, and teeth on one side of the mouth to teeth on the other side of mouth.

These drawbacks are particularly troublesome when preparing teeth within the mouth for restoration with splinted teeth or multiple unit bridges. In these cases, the surfaces of the teeth must be prepared by grinding or filing, such that the bridge will have a clear "line of draw", or "path of insertion". To have a clear path of insertion, the teeth must be ground or filed such that they have a substantially truncated pyramidal shape. This will allow the bridge to slip on and off easily. Hence it is important that corresponding surfaces of different teeth are ground or filed such that there upward and inward taper is approximately the same. Equally important, is the fact that the teeth should not be over prepared in order to conserve tooth structure, and reduce the changes for later root canal therapy.

SUMMARY OF THE INVENTION

Accordingly, it is an object of this invention to provide a dental path of insertion guide which can be used both inside and outside of the mouth.

Another object is to provide such a guide which can be used with many teeth at the same time.

Another object is to provide a dental guide which can be used on two related multiple surfaces of multiple teeth over short or large edentulous spans.

Another object is to provide a visual aid which will help in determining whether there is a clear path of insertion.

Another object of this invention is to provide a device which can easily be customized for various tooth combinations.

Another object of this invention is to provide a device having pins which can be easily added or removed, and which can be easily inverted to relate opposing arches, such as in orthodontics.

The foregoing objects are basically obtained by a dental path of insertion guide comprising an elongated member which has first and second ends, a handle coupled to the elongated member, at least one cap which is releasable coupled to either the first or second end, at least four substantially parallel straight pins, each having a first and second end, and at least four supports, each support rigidly coupled to one of the pins at the first end, and slidably coupled to the elongated member.

Other objects, advantages and salient features of the present invention will become apparent from the following detailed description, which, taken in conjunction with the annexed drawings, discloses preferred embodiments of the invention.

DRAWINGS

Referring now to the drawings which form a part of this original disclosure:

FIG. 1 is a front elevational view of a dental path of insertion guide in accordance with the present invention;

FIG. 2 is a bottom plan view of the dental path of insertion guide shown in FIG. 1;

FIG. 3 is a right perspective view in transverse section of the path of insertion guide of FIG. 1 taken along line 3—3 in FIG. 1;

FIG. 4 is a right perspective view of a support and pin which is used in the path of insertion guide of FIGS. 1 and 2;

FIG. 5 is a side elevational view of two teeth having an edentulous span therebetween;

FIG. 6 is a side elevational view of the two teeth of FIG. 5, which have been prepared by filing or grinding so that they have a substantially truncated pyramidal shape, and a dental path of insertion guide in accordance with the invention which has been placed over the teeth and the pins aligned adjacent to the teeth so that the upward and inward taper of the teeth may be visually inspected;

FIG. 7 is a top plan view of a full-mouth dental path of insertion guide in accordance with the invention;

FIG. 8 is a bottom plan view of a half-mouth dental path of insertion guide in accordance with the present invention;

FIG. 9 is a front elevational view in section of the elongated member of FIG. 7 taken along the line 9—9;

FIG. 10 is a front elevational view in section of a support and pin shown in FIG. 7 taken along line 10—10, the sectional view of the elongated member shown in FIG. 9 having been removed;

FIG. 11 is a side elevational view in section of the pin and support of FIG. 10 taken along line 11—11;

FIG. 12 is a side elevational view showing the use of a dental path of insertion guide in accordance with this invention to visually compare the preparation of two upper teeth and one lower tooth; and FIG. 13 is a front elevational view of a path of insertion guide being used to compare tooth surfaces on different sides of the mouth.

DETAILED DESCRIPTION OF THE INVENTION

As seen in FIGS. 1 and 2, a path of insertion guide 14 comprises an elongated member 16 having first and second ends 17 and 19, a handle 18 attached to the first end 17, supports 20, 22, 24, and 26 which are slidably coupled to the elongated member 16, and parallel pins 28, 30, 32, and 34 which are rigidly attached to the supports. The second end 19 of elongated member 16 has threads 36 thereon, which are threadedly received by internal threads 38 in cap 40.

Referring now to FIGS. 3 and 4, elongated member 16 is shown having a rectangular transverse cross section which corresponds approximately to the configuration of the throughbore 42 in support 26. By having a similarly configured throughbore 42, support 26 is capable of slidably coupling to elongated member 16, but is incapable of relative rotational movement about the central longitudinal axis of elongated member 16. Also, the rectangular configuration allows the support 26 to be slidably coupled onto the elongated member 16 such that pin 34 may be either extending upwardly or downwardly from the elongated member 16.

As seen in FIG. 4, pin 34 has first and second ends 35 and 37, the first end 35 being rigidly coupled to support 26 and the second end 37 being free. The remaining pins are likewise constructed and can be of different lengths as desired.

The path of insertion device shown in FIGS. 1–4 may be comprised of any material, such as stainless steel, or a polymeric material, but is advantageously constructed of a material which is capable of being easily sterilized. Advantageously, the pins are constructed of a material which is easily cut, thereby facilitating quick customization of the pin length. The pins can be integrally formed with the supports or adhered thereto. Quick and easy customization is especially helpful when dealing with posterior teeth. Since the pin-containing supports may be easily added to or removed from the elongated member, a shortened pin may be kept and reused in situations where a shorter pin is desired. Alternatively, the pins can be manufactured in various lengths, in which case they would just be chosen as needed.

While FIGS. 1 and 2 show a path of insertion guide having four supports, any number of supports is contemplated. Additional pin-containing supports may be added simply by uncoupling cap 40 and adding more.

Also, while a rectangular configuration for elongated member 16 is shown, many other configurations would be suitable. Advantageous configurations, would be those in which the support could be slidably coupled to the elongated member such that the pin could be maintained in either a vertically upwardly or vertically downwardly extending position with no possibility for relative rotational movement by the support about the central longitudinal axis of the elongated member.

FIGS. 5 and 6 illustrate an application of the path of insertion guide shown in FIGS. 1–4.

In FIG. 5, a gum 44 having teeth 46 and 48, and an edentulous span 47 is shown before preparation for bridgework. The same gum and teeth are shown in FIG. 6 after preparation for bridgework by grinding or filing the surfaces of teeth 46 and 48 to an approximately truncated pyramidal shape, i.e., upwardly and inwardly tapering sides and a substantially flat top surface. When the path of insertion guide 14 is placed above the teeth 46 and 48, the pins 28, 30, 32 and 34 which extend downwardly from the elongated member 18 to the gum 44 allow a visual inspection of the angles of the upwardly inwardly tapered surfaces of the teeth, a, a', b, and b'. For there to be a clear path of insertion, angles a and a' must be approximately parallel, and angles b and b' must be approximately parallel. Only then will bridgework be able to easily slip on and off of the prepared teeth 46 and 48. It should be noted that angles a, and a', b, and b', should be only about 6° to help conserve tooth structure and thereby minimize the chances for later-needed root canal therapy.

Referring now to FIGS. 7–11, additional embodiments of the present invention are shown.

In FIG. 7, a full-mouth path of insertion guide 50 is shown having handle 52 located on or about the middle of the approximately U-shaped elongated member 54, caps 56 and 58 which are threadedly connected to each end of the elongated member 54, and supports 60, 62, 64, 66, 68, 70, 72, and 74. This full-mouth embodiment of the path of insertion guide is useful when it is desired to relate the surfaces of teeth which are on opposite sides of the mouth. While only four supports are shown on each side, any amount up to about 17 supports per full-mouth guide are contemplated.

FIG. 8 is a half-mouth path of insertion guide, which is used when the surfaces of teeth on only one side of the mouth are to be examined. As seen in FIG. 8, the half-mouth path of insertion guide 76 is comprised of handle 78 located at the end of the arcuate-shaped elongated member 80, cap 82 which is threadedly connected to elongated member 80, and supports 84, 86, 88, and 90 having pins 92, 94, 96, and 98 rigidly coupled thereto, respectively. The half-mouth guide can contain up to about nine supports.

The full-mouth and half-mouth path of insertion guides can be constructed from the same materials as the approximately straight path of insertion guide shown in FIGS. 1 and 2, i.e., a material which may be easily sterilized and easily cut.

These embodiments are especially advantageous when preparing, for example, a "Roundhouse" bridge. When preparing a "Roundhouse", substantially all the teeth in either the upper or lower arch require preparation. This is especially difficult since the surfaces of the front teeth, which have a central longitudinal axis extending forwardly from the gum, must be composed with the surfaces of the posterior teeth, which have a central longitudinal axis extending rearwardly from the gum and toward the cheek. In order to have a clear path of insertion, the buccal, ligual, mesial, and distal surfaces of each prepared tooth must be approximately parallel. A full-mouth or half-mouth guide enables the practitioner to compare these surfaces simultaneously within the patient's mouth. This aids the practitioner in determining whether there is a clear path of insertion, and decreases the likelihood of overpreparation.

While the full-mouth and half-mouth paths of insertion guides are shown having approximately elliptically shaped elongated members, any curved configuration which approximates the curvature of the mouth is contemplated, such as, for example, semi-circular, parabolic, etc. Also, the path of insertion guides can be made in numerous sizes to accommodate any size mouth encountered.

Since the full-mouth and half-mouth path of insertion guides 50 and 76 have curved elongated members, a specially shaped support is required, i.e., a support is required which will be able to negotiate the curves of the elongated member. While any design which will allow the support to negotiate the curves of the elongated member is contemplated, an advantageous configuration for the elongated member and support are shown in FIGS. 9–11.

As seen in FIG. 9, elongated member 54 has approximately diametrically opposed outwardly-facing grooves 55 and 57 positioned approximately on the sides of the elongated member 54, and approximately flat surfaces 59 and 61 positioned approximately at the top and bottom of elongated member 54.

As seen in FIG. 10, support 74 is shown having inwardly-facing tongues 77 and 79 which are slidably received in the grooves 55 and 57 of elongated member 54. The support 74 also has approximately flat top and bottom inside surfaces 81 and 83 which complement the flat surfaces of 59 and 61 of the elongated member 54.

As seen in FIG. 11, support 74 also has pairs of stabilizing members 85 and 87 which extend outwardly from the support in both directions and are of the same width as the approximately flat surfaces 59 and 61 of elongated member 54. Also, as seen in FIG. 11, except for the stabilizing members 85 and 87, the body of support 74 is approximately of the same width as the pin 75 which is rigidly coupled to the support 74.

The design of the elongated member and supports shown in FIGS. 7–11 is advantageous for a number of reasons.

First, the grooves 55 and 57 which slidably receive tongues 77 and 79 insure that there will be no relative rotational movement by the support 74 around the central longitudinal axis of the elongated member 54. Since two approximately diametrically opposed grooves are provided, the support may be slidably coupled such that the pins are extending vertically upwardly or downwardly from the elongated member 54.

Second, the relatively narrow width of the support 74, except for the stabilizing members 87 and 85, allows the support 74 to slide easily along the curved elongated member 54. It could be easily recognized that a support having a wide body would be very difficult, indeed, to slide around a curved surface. However, the stability which would be inherent in a wide body support is achieved by use of stabilizing members 85 and 87. These members are approximately the same width as the approximately flat surfaces 59 and 61 and extend along the surfaces of the elongated member in both directions for a short distance. This provides the support 74 with the stability needed to maintain the pin in the substantially vertical position, yet provides the support 74 with the ability to easily negotiate the curves of the elongated member.

Referring now to FIG. 12, the path of insertion guide 106 can be a straight path of insertion guide as shown in FIGS. 1 and 2, or a full-mouth embodiment as shown in FIG. 7, or a half-mouth embodiment as shown in FIG. 8. As seen in FIG. 12, the path of insertion guide 106 is used to visually compare the surfaces of teeth 102 and 104 in the upper gum 100 with the surfaces of tooth 105 in the lower gum 101. The path of insertion guide 106 is comprised of elongated member 108 having supports thereon 110, 112, 114, 116, 118, and 120, with pins 122, 124, 126, 128, 130, and 132 rigidly coupled thereto. Cap 134 is coupled to the end of elongated member 108. As can be seen, the path of insertion guide 106 provides for visual inspection of the corresponding angles c and c'; and d and d', of teeth 102 and 104, while at the same time providing visual inspection of the angle e and f of tooth 105.

Referring now to FIG. 13, a path of insertion guide 140 is shown being used to compare tooth surfaces of a model or mold 142. It should be noted, that while the path of insertion guides disclosed in this invention are especially advantageous because of their ability to be used inside the mouth, they are equally advantageous for use on plaster molds or models outside of the mouth, such as for example, in laboratory or classroom situations.

As seen in FIG. 13, path of insertion guide 140 is shown having elongated member 144, supports 146, 148, 150, 152, and 154, which are rigidly coupled to pins 156, 158, 160, 162 and 164, respectively. The cap is shown as comprising two threaded nuts 166 and 168 which are threadedly coupled to elongated member 144.

The use of the relatively straight elongated member 144 in FIG. 13 allows comparison of the buccal and lingual surfaces of the teeth at the same time, even across the arch. If a full-mouth or half-mouth guide were instead used, the mesial and distal surfaces could be inspected.

While several advantageous embodiments have been chosen to illustrate the invention, it will be understood by those skilled in the art that various changes and modifications can be made therein without departing from the scope of the invention as defined in the appended claims.

What is claimed is:

1. A dental path of insertion guide, the combination comprising:
   an elongated member having first and second ends;
   a handle coupled to said elongated member;
   at least one cap releasably coupled to at least one of said first and second ends;
   at least four substantially parallel straight pins, each having first and second ends; and
   at least four supports, each support rigidly coupled to one of said pins at said first end, and each of said supports being slidably coupled to said elongated member.

2. The guide of claim 1, wherein
   said handle is coupled to said first end of said elongated member.

3. The guide of claim 1, wherein
   said elongated member is substantially straight.

4. The guide of claim 1, wherein
   said second end has external threads; and
   said cap has internal threads, such that said cap may be releasably coupled to said second end.

5. The guide of claim 1, and further comprising
   means, provided on said elongated member and on each of said supports, for sliably coupling each of said supports to said elongated member and for preventing relative rotational movement of the support about the central longitudinal axis of said elongated member, and for maintaining each of said pins parallel to one another.

6. The guide of claim 5, wherein
   said means include at least one groove, and at least one tongue, which is slidably received in said at least one groove.

7. The guide of claim 6, wherein
   said elongated member has a substantially circular transverse cross section.

8. The guide of claim 6, wherein said elongated member has a substantially polygonal cross section.

9. The guide of claim 1, wherein said elongated member has a substantially polygonal cross section.

10. The guide of claim 1, wherein said elongated member is substantially U-shaped.

11. The guide of claim 10, wherein said handle is coupled to said U-shaped elongated member at substantially the middle thereof.

12. The guide of claim 1, wherein said elongated member is substantially arcuate.

13. The guide of claim 12, wherein said handle is coupled to said arcuate elongated member at the end thereof.

14. The guide of claim 1, wherein each of said supports has a substantially rectangular throughbore, and said elongated member has a substantially rectangular cross section.

* * * * *